United States Patent [19]

Handy

[11] Plant 4,444

[45] Jul. 31, 1979

[54] DOGWOOD TREE

[76] Inventor: Glen E. Handy, Rte. 2, Box 347, Troutdale, Oreg. 97060

[21] Appl. No.: 923,086

[22] Filed: Jul. 10, 1978

[51] Int. Cl.[2] ..... A01H 5/00
[52] U.S. Cl. ..... Plt./51
[58] Field of Search ..... Plt./51

*Primary Examiner*—Robert E. Bagwill

*Attorney, Agent, or Firm*—Klarquist, Sparkman, Campbell, Leigh, Hall & Whinston

[57] ABSTRACT

This invention relates to a novel variety of flowering dogwood tree, distinguished by unusually large leaves, a majority of which have a generally centrally oriented sharply defined light colored area and a dark colored margin, white flowers with red tips, the flowers typically appearing when the tree is quite young, upright habit of growth and brilliant dark red Fall leaf color.

4 Drawing Figures

DESCRIPTION

The present invention relates to a new and distinct variety of flowering dogwood tree of the species botanically known as *Cornus florida.*

My new variety originated as a bud sport of a *Cornus florida welchii* tree which I was growing on cultivated property in my nursery at Portland, Oreg. My attention was drawn to this particular tree because of its unusually large leaves, in comparison with other dogwood trees of the same species growing in the same area, and because of the multi-coloration of its leaves. These characteristics exhibited by this tree, the parent tree of my new variety, had never previously been exhibited in any *Cornus florida* tree of which I was aware.

Closer observation of the parent tree, and continued observation of progeny thereof, which possessed identical characteristics so far as observable, and which were subsequently asexually propagated under my direction in Portland, Oreg., by budding to *Cornus florida* understock, has convinced me that my new tree represents a new and improved variety of *Cornus florida.* Furthermore, these observations have confirmed that my new variety is particularly evidenced by the following unique combination of characteristics, which have proven firmly fixed, are outstanding therein, and which distinguish it from all other varieties of this species:

1. A centrally oriented sharply defined light green to yellow central area on a majority of the leaves;
2. Extremely large leaves;
3. Blooms which first appear on the trees when they are unusually young;
4. Flower petals which have a red tip;
5. Upright habit of growth; and
6. Brilliant dark red Fall colors.

The accompanying photographs depict the color of the foliage and flowers of my new variety as nearly true as is reasonably possible to make the same in a color illustration of this character.

FIG. 1 is a color photograph of an entire tree of the present invention, taken in late June 1977 to show the upright habit of growth of the tree;

FIG. 2 is a closeup photograph of leaves of a tree of my variety, taken at the same time as the photograph of FIG. 1 to show the light colored central area of the leaves;

FIG. 3 is a color photograph of a flower of my new variety, taken in late April 1978 to show the red tip of the petals; and FIG. 4 is a color photograph of leaves of the tree of my invention, taken in November 1977 to show their brilliant Fall colors.

One distinguishing characteristic of my tree is a sharply defined green to greenish-yellow central area of the majority of leaves of each tree. The remainder of the leaves are a dark green color so that my tree exhibits, during the Spring and Summer, striking multi-colored leaves. Although known *Cornus florida welchii* leaves are variegated, the central area of such leaves is almost white, and not the green to green-yellow color of the central area of the multi-colored leaves of my tree. In addition, the leaves of my tree are also much larger than those of *Cornus florida welchii* trees. In many cases, the leaves of my variety appear to be approximately twice as large as the leaves of other varieties of this species. More specifically, a number of leaves from my tree, selected at random during November 1977, were found to range from approximately 6 to 10.7 centimeters wide and from approximately 10.7 to 17.7 centimeters long.

Also, flowers often begin appearing on trees of my new variety during the second year after they have been budded. On the other hand, *Cornus florida welchii* trees do not bloom until their third or fourth year from budding, and often not until their fifth or sixth year. Unlike other known varieties of this species, the flowers of my new variety are white with many of the petals having a red tip.

In addition, my new dogwood tree has upright branches in comparison to the more spreading growing habit of branches of other dogwood trees of this species.

Furthermore, the Fall colors of my variety appear to be a more brilliant dark red color than the red Fall colors more typical of the species.

Otherwise, insofar as I have been able to observe at this time, my new variety is generally typical of the species.

Following is a detailed description of my new variety of *Cornus florida* tree with color terminology in accordance with the *Royal Horticultural Society Color Chart* (hereinafter RHS) published by the Royal Horticultural Society of London. It is pointed out, however, that the coloration of the leaves as indicated below is only approximate because the coloration varies considerably depending upon lighting conditions and time of year. In addition, the size and shape of the leaves varies depending upon the nature of the growing season.

Parentage: A bud sport of *Cornus florida welchii.*

Propagation: Holds to distinguishing characteristics through succeeding propagation by budding on *Cornus florida* understock.

Locality where grown and observed: Portland, Oreg.

Tree: Upright habit of growth, healthy.

Foliage:

*Shape.*—Ovate, with some leaves being broader than others.

*Apex.*—Acuminate.

*Base.*—Obtuse.

*Margin.*—Entire.

*Size.*—Length, in one sampling the length of leaves ranged from about 10.7 centimeters to 17.7 centimeters from the base of the petiole to the tip of the leaf and averaged approximately 14.8 centimeters. Width, in the above sampling the width of the leaves ranged from about 6 centimeters to about 10.7 centimeters and averaged approximately 8.7 centimeters.

*Color.*—In early Summer, the leaves are two colored with a dark green colored margin like RHS Plate 137A and a central lighter colored area which is a greenish-yellow to yellow color like RHS Plate 144A. In the Fall, the leaves turn a brilliant red color somewhat darker than RHS plate 183A.

Flowers:

*Color.*—White with many of the petals having tips which are a red color like RHS Plate 183A.

I claim:

1. A new and distinct variety of flowering dogwood tree substantially as herein shown and described, characterized particularly as to novelty by unusually large leaves with a majority of the leaves having a dark colored margin and a light colored sharply defined central area, blooms which typically appear when the tree is extremely young, many petals of the blooms having a red tip, an upright habit of growth and brilliant dark red Fall leaf color.

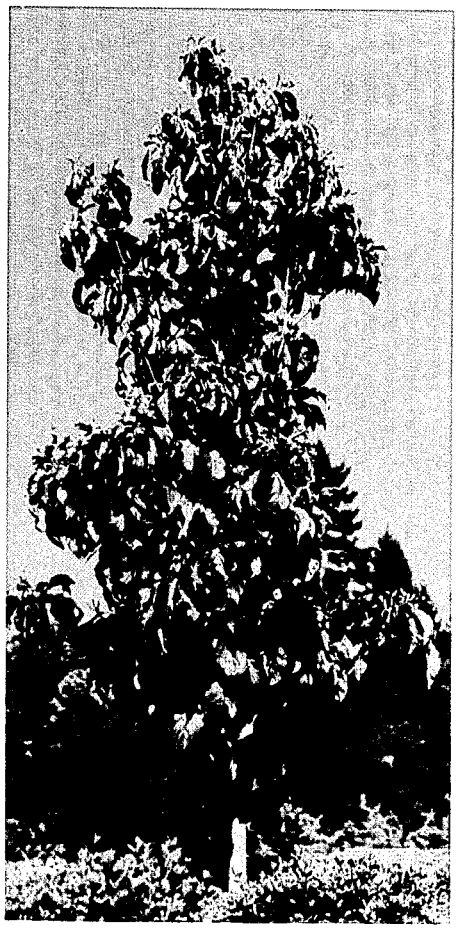
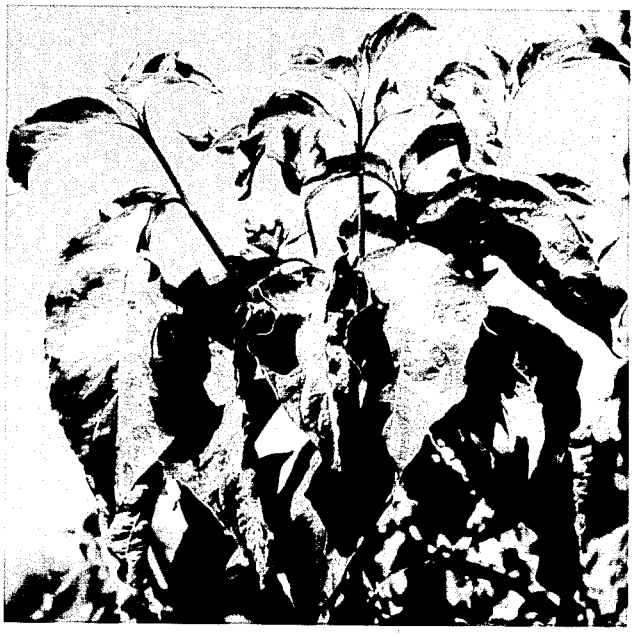
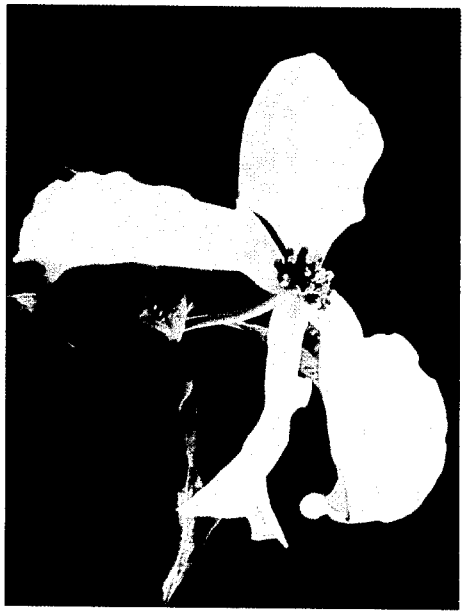
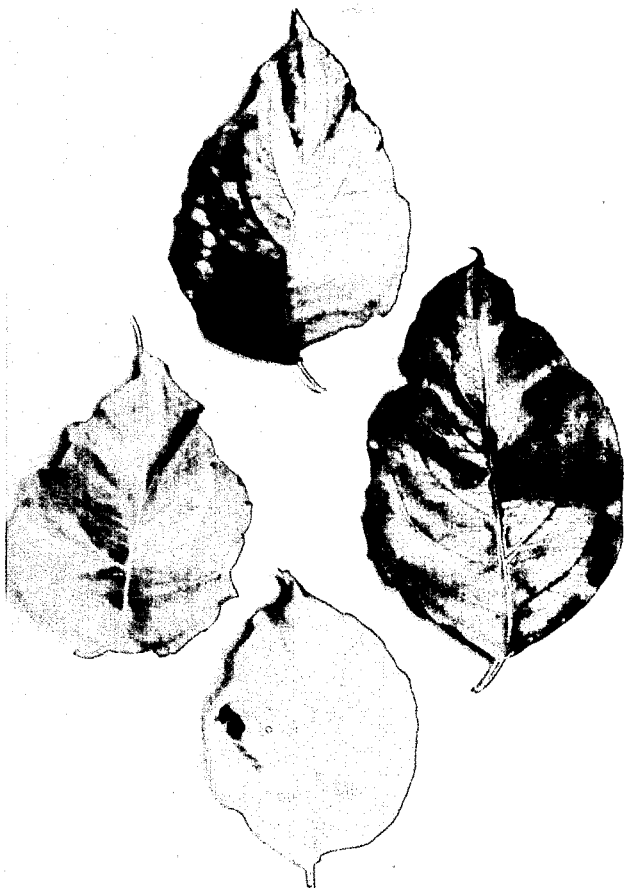

* * * * *